(12) United States Patent
Douglas et al.

(10) Patent No.: US 8,702,681 B2
(45) Date of Patent: Apr. 22, 2014

(54) CATHETER VALVE AND METHODS OF USING SAME

(75) Inventors: Peter F. Douglas, Newtown Square, PA (US); Emily Y. Ho, Wayne, PA (US); Vinu J. Zachariah, Kochi (IN); Arvind Mathivathanan, Chennai (IN); Arpita Banerjee, Bangalore (IN); Sanjeeb K. Behera, Chennai (IN); Kiran P. Devapalan, Bangalore (IN); Michael C. Mochahari, Bangalore (IN); Rajkumar Palanivel, Bangalore (IN); Gopinath Ravindranath, Chennai (IN); Muthamizhselvan Muthusamy, Perambalur Taluk & District (IN)

(73) Assignee: Progeny Concepts, LLC, Newtown Square, PA (US)

( * ) Notice: Subject to any disclaimer, the term of this patent is extended or adjusted under 35 U.S.C. 154(b) by 0 days.

(21) Appl. No.: 13/485,127

(22) Filed: May 31, 2012

(65) Prior Publication Data

US 2013/0324975 A1    Dec. 5, 2013

(51) Int. Cl.
*A61B 19/00*    (2006.01)

(52) U.S. Cl.
USPC ............. 604/544; 137/15.23; 251/9; 251/193

(58) Field of Classification Search
USPC ....................................................... 604/544
See application file for complete search history.

(56) References Cited

U.S. PATENT DOCUMENTS

| | | | |
|---|---|---|---|
| 1,959,074 A | 5/1934 | Bloxsom | |
| 2,595,511 A | 5/1952 | Butler | |
| 3,099,429 A | 7/1963 | Broman | |
| 4,306,705 A | 12/1981 | Svensson | |
| 4,492,258 A | 1/1985 | Lichtenstein et al. | |
| 4,497,468 A | 2/1985 | Hubbard et al. | |
| 4,662,599 A | 5/1987 | Attermeier | |
| 4,815,477 A * | 3/1989 | McWhorter et al. | 600/579 |
| 5,090,424 A | 2/1992 | Simon et al. | |
| 5,156,603 A | 10/1992 | Olsen | |

(Continued)

FOREIGN PATENT DOCUMENTS

| | | |
|---|---|---|
| DE | 3324699 C1 | 12/1984 |
| EP | 0948971 A1 | 10/1999 |

(Continued)

OTHER PUBLICATIONS

"Desiccants". Medical Systems for Industry. <http://www.medicalsysforindustry.com/desiccants.html>. Aug. 2008.*

(Continued)

*Primary Examiner* — Leslie Deak
*Assistant Examiner* — Sara Sass
(74) *Attorney, Agent, or Firm* — Barley Snyder

(57) ABSTRACT

A valve having a valve body with a first end, a second end, a longitudinal axis extending between the first end and the second end, and an inclined sliding surface having a longitudinal slot therein. The valve also includes a tubular member with walls defining a passageway extending through the valve body from the first end to the second end; and a slidable member mounted on the valve body and moveable between a first position and a second position. The slidable member is adapted to urge walls of the tubular member towards mutual contact when moved from the first position to the second position.

39 Claims, 13 Drawing Sheets

(56) References Cited

U.S. PATENT DOCUMENTS

| | | |
|---|---|---|
| 5,195,997 A | 3/1993 | Carns |
| 5,713,877 A | 2/1998 | Davis |
| 5,902,294 A | 5/1999 | Edwards |
| 6,106,503 A | 8/2000 | Pfeiderer et al. |
| 6,162,201 A * | 12/2000 | Cohen et al. ............... 604/250 |
| 6,913,244 B1 | 7/2005 | Atkinson et al. |
| 7,186,245 B1 | 3/2007 | Cheng et al. |
| 7,211,074 B2 | 5/2007 | Sansoucy |
| 7,547,298 B2 | 6/2009 | Lee et al. |
| 7,828,269 B2 | 11/2010 | Iversen |
| 7,833,169 B2 | 11/2010 | Hannon |
| 7,850,677 B2 | 12/2010 | Blake et al. |
| 7,875,021 B2 | 1/2011 | Minassians |
| 7,938,807 B2 | 5/2011 | House |
| 8,025,651 B1 | 9/2011 | Hart |
| 8,083,728 B2 | 12/2011 | Rome |
| 2006/0095019 A1 | 5/2006 | Dikeman et al. |
| 2008/0029721 A1 * | 2/2008 | Miyahara ........................ 251/6 |
| 2009/0030378 A1 | 1/2009 | Garcia, Jr. |
| 2010/0274174 A1 | 10/2010 | Swisher |
| 2010/0331825 A1 | 12/2010 | Hakky et al. |
| 2011/0071506 A1 | 3/2011 | Gardner et al. |
| 2011/0082444 A1 | 4/2011 | Mayback et al. |
| 2011/0213345 A1 | 9/2011 | House |

FOREIGN PATENT DOCUMENTS

| | | |
|---|---|---|
| GB | 2042131 A | 9/1980 |
| GB | 2271829 A | 4/1994 |
| WO | 94/14497 A1 | 7/1994 |
| WO | 2009/046176 | 4/2009 |
| WO | 2010/041084 | 4/2010 |
| WO | 2011/091798 | 8/2011 |
| WO | 2011/140600 | 11/2011 |

OTHER PUBLICATIONS

Int'l Search Report dated Aug. 29, 2013 issued in corresponding Int'l Appln. No. PCT/US2013/038406.

* cited by examiner

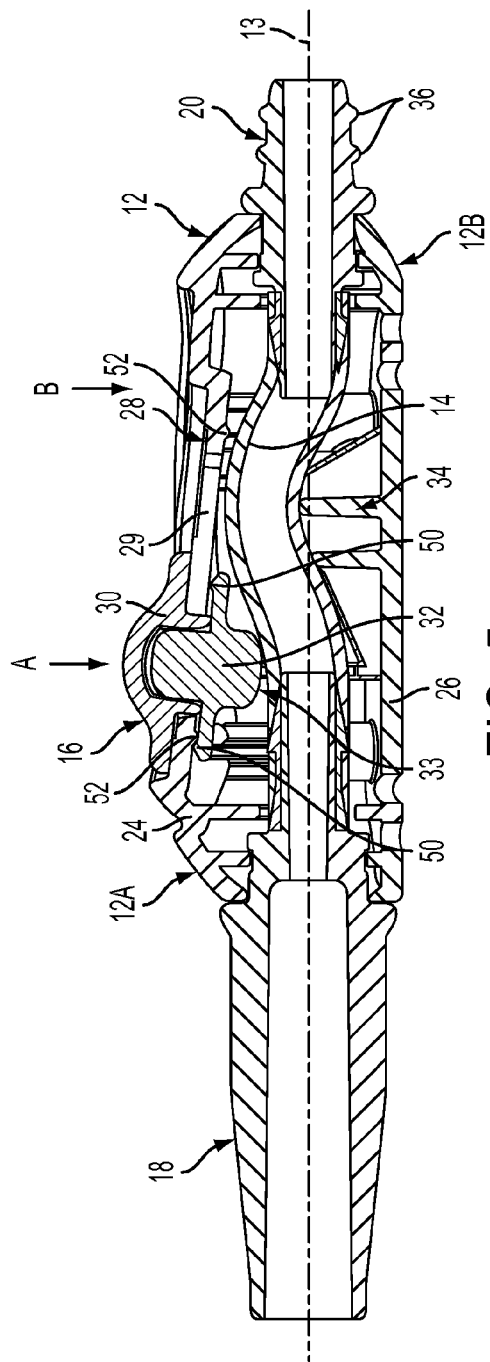

CATHETER VALVE AND METHODS OF USING SAME

TECHNICAL FIELD

Embodiments of the present invention relate to a valve for restricting the flow of a fluid therethrough, application of the valve to urinary catheters, and methods of using the valve.

BACKGROUND

Catheters, particularly indwelling and suprapubic catheters, are commonly prescribed for patients that are unable to void their bladders without assistance. Such catheters comprise a tube placed through the urethra and into the bladder, which allows urine to continuously flow from the bladder. Because the flow of urine from the bladder is continuous, in order to prevent leakage and to collect urine, a collection device, such as, for example, a urine bag, or another device such as a valve, must be constantly in place on the external end of the catheter. However, use of a urine bag is not desirable because if a user wishes to remain mobile, the bag typically must be attached to a user's leg, which can be uncomfortable because of the bag's bulky nature both before and after it is filled. Also, its bulky nature makes it visible when worn with every day clothes. Because a user who is mobile is constantly moving, there is also the potential for the urine bag to leak or even worse, disconnect while in use, which may result in an embarrassing situation for the user. Moreover, prior valves have been complicated structures that require a wearer to use two hands or require great dexterity to actuate.

Accordingly, there is a need for a device that can be used with a catheter to void the bladder that is discrete, resistant to leakage, easy to use, and comfortable when used in everyday life.

SUMMARY

We provide a valve having a valve body with first and second ends and an inclined sliding surface with a longitudinal slot therein, a tubular member with a passageway therein extending through the valve body from the first end to the second end of the valve body, and a slidable member mounted on the valve body and moveable between a first position and a second position. Movement of the slidable member along the inclined sliding surface from the first position to the second position causes the slidable member to urge walls of the tubular member towards mutual contact whereby the flow of fluid through the tubular member is restricted. In contrast, movement of the slidable member along the inclined sliding surface from the second position to the first position allows the walls to separate whereby the flow of fluid through the tubular member is permitted.

We also provide a urinary catheter valve assembly for controlling the flow of urine from the bladder, the catheter valve having a valve body with first and second ends and an inclined sliding surface with a longitudinal slot therein, a tubular member with a passageway therein extending through the valve body from the first end to the second end of the valve body, and a slidable member mounted on the valve body and moveable between a first position and a second position. Movement of the slidable member along the inclined sliding surface from the first position to the second position causes the slidable member to urge walls of the tubular member towards mutual contact whereby the flow of urine through the tubular member is restricted. In contrast, movement of the slidable member along the inclined sliding surface from the second position to the first position allows the walls to separate whereby the flow of urine through the tubular member is permitted.

We also provide a catheter assembly comprising a catheter having a proximal end, for insertion into a patient and a distal end adapted to extend outside of the patient, and a catheter valve. The catheter valve includes a valve body and an inclined sliding surface with a longitudinal slot therein, a tubular member with a passageway therein extending through the valve body, and a slidable member mounted on the valve body and moveable between a first position and a second position. Movement of the slidable member along the inclined sliding surface from the first position to the second position causes the slidable member to urge walls of the tubular member towards mutual contact whereby the flow of urine through the tubular member is restricted. In contrast, movement of the slidable member along the inclined sliding surface from the second position to the first position allows the walls to separate whereby the flow of urine through the tubular member is permitted.

We also provide a kit comprising a catheter and a catheter valve having a valve body, a tubular member extending through the valve body, a slidable member mounted on the valve body and moveable between a first position and a second position.

For a better understanding of the embodiments of the present invention, its operating advantages and specific objects attained by its uses, reference is made to the accompanying descriptive matter in which preferred embodiments of the invention are illustrated in the accompanying drawings.

BRIEF DESCRIPTION OF THE DRAWINGS

FIG. 5 is a cross-sectional view taken along line A-A in FIG. 1, with the catheter valve shown in the open position.

FIG. 6 is a cross-sectional view taken along line A-A in FIG. 1, with the catheter valve shown in the closed position.

DETAILED DESCRIPTION

Figure 1:
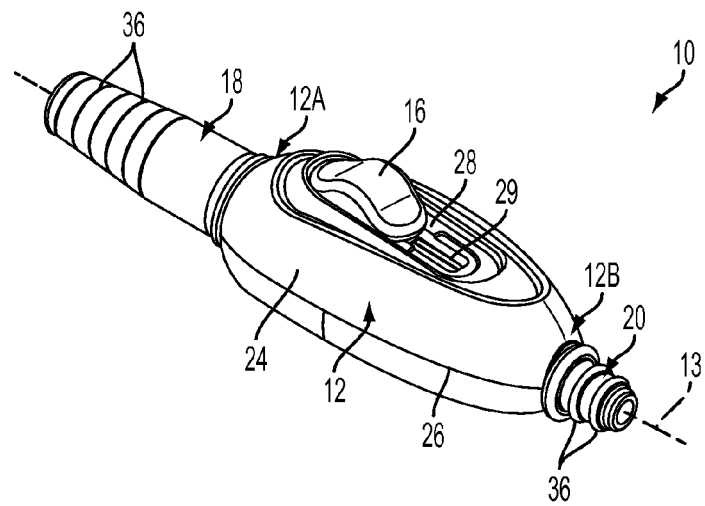
FIG. 1 is a perspective view of an exemplary embodiment of a catheter valve.

In the figures, in which like numerals indicate like elements throughout, there is shown an embodiment of a catheter valve. The catheter valve is generally referred to by the numeral 10. The catheter valve 10 is preferably low-profile and allows the user or caregiver to selectively control the flow of urine from a catheter. Such a catheter can be, for example, a Foley-type catheter. This selective restriction of urine flow permits temporary sealing of the catheter without the need to be constantly tethered to a collection device such as a urine bag. Accordingly, a user can achieve improved mobility and comfort by temporarily detaching the collection device without either having to remove the catheter from the bladder or risking leakage. In other cases, the valve 10 provides a user with increased mobility without the need for a collection device, by permitting the user to drain the catheter directly into a toilet or other receptacle through operation of the catheter valve 10. As used herein, the terms "proximal" and "distal" refer to the portions of a device that are closest to and further away from an attending physician during insertion into a patient. For example, with respect to a catheter, such as a Foley catheter, the distal end of the catheter is inserted into the patient's bladder, and the proximal end of the catheter remains outside of the patient after insertion.

Depicted in FIGS. 1 through 9 is a first exemplary embodiment of the catheter valve 10. As shown in the figures, the catheter valve 10 comprises a valve body 12 having an inlet end 12A, an outlet end 12B, a longitudinal axis 13, a tubular member 14 (see FIGS. 5-9), which includes a lumen that defines a passageway therethrough, a slidable member 16, an inlet connector 18 on the inlet end 12A of the valve body 12, and an outlet connector 20 on an outlet end 12B of the valve body 12. In the present embodiment, the valve body 12 is a two-piece structure that includes a top portion 24 and a bottom portion 26, which can be joined together using any means known in the art including a snap or press-fit connection, adhesive connection, ultrasonic welding, etc. In alternative embodiments, the valve body may be a unitary structure.

Figure 2:
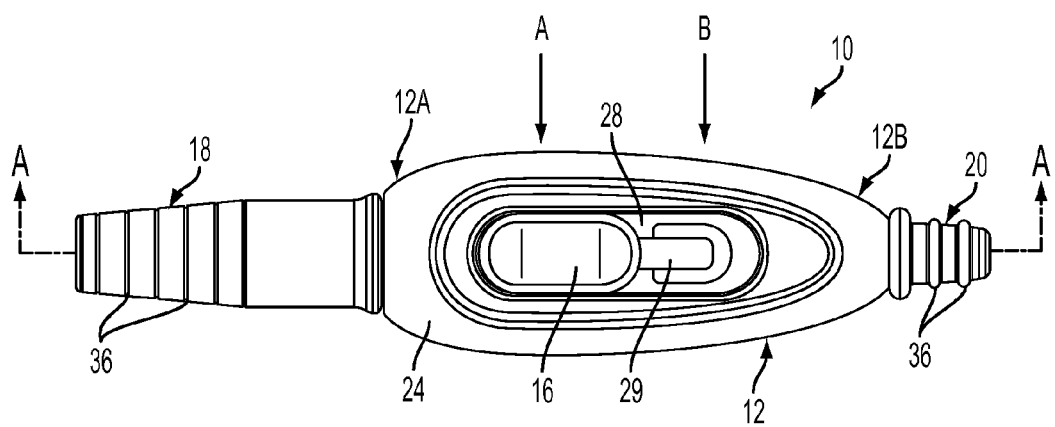
FIG. 2 is a top plan view of the catheter valve depicted in FIG. 1.
Figure 3:
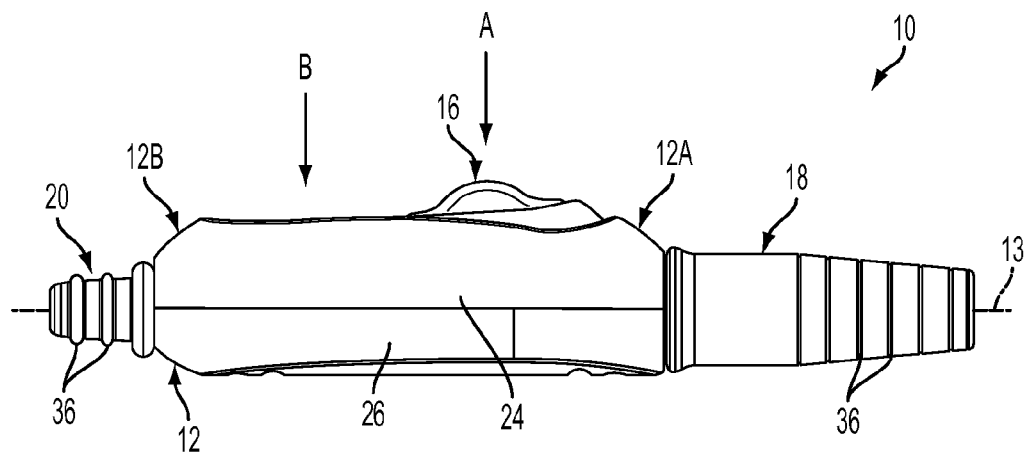
FIG. 3 is side view of the catheter valve depicted in FIG. 1.
Figure 4:
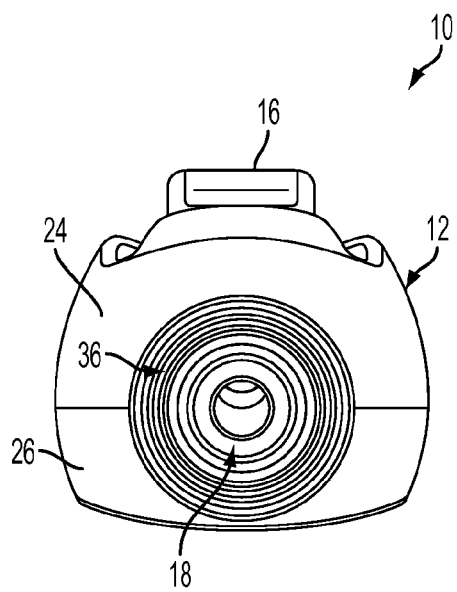
FIG. 4 is an end view of the catheter valve depicted in FIG. 1.
Figure 7:
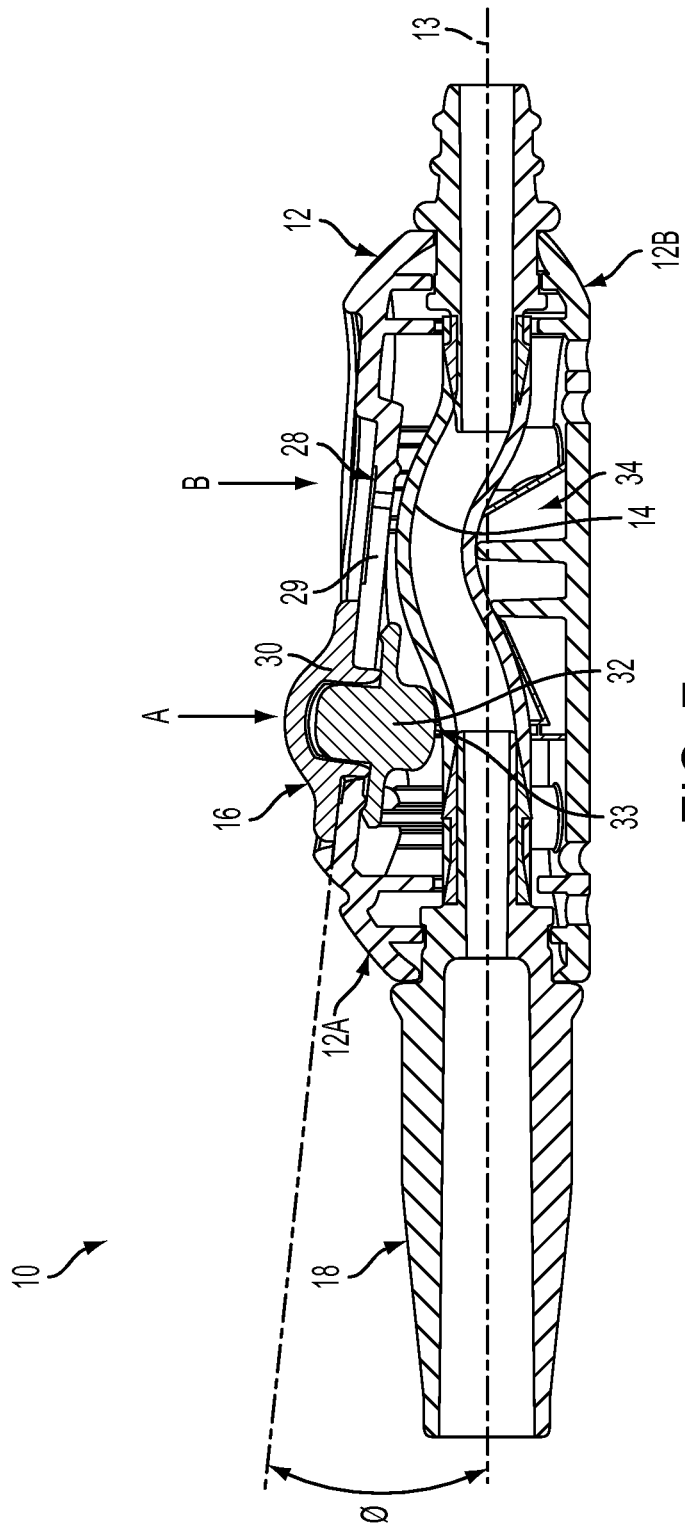
FIG. 7 is a further cross-sectional view taken along line A-A in FIG. 1, with the catheter valve in the opened position.

As can best be seen in FIGS. 5-7, the top portion 24 of the valve body 12 includes an inclined sliding surface 28 upon which the slidable member 16 is mounted. The inclined sliding surface 28 inclines at an angle "θ," which may preferably range from approximately 1° to 45° with respect to the longitudinal axis 13, from the outlet connector 20 to the inlet connector 18. The inclined sliding surface 28 includes a longitudinal slot 29 therein that is substantially parallel to the longitudinal axis 13 of the valve body 1 when viewed from above, such as is depicted in FIG. 2. The longitudinal slot 29 forms a track that permits the slidable member 16 to be operable between a first, open position (position "A" in the figures, see FIG. 5) and a second, closed position (position "B" in the figures, see FIG. 6) thereby allowing the user or caregiver to selectively operate the catheter valve 10 between the open and closed position to allow or restrict the flow of a fluid, such as urine, through the catheter valve 10 (further operation of the catheter valve 10 will be discussed below). As can be seen in FIGS. 5 and 6, the inclined sliding surface 28 is at a maximum height above the interior base of the valve body 12 at position "A" and at a minimum height above the base at position "B." Preferably, the angle "θ" of the inclined surface 28 with respect to the longitudinal axis 13 ranges from approximately 3° to approximately 10°.

Although the inclined sliding surface 28 and the longitudinal slot 29 are depicted as being substantially straight and substantially aligned to the longitudinal axis 13, as best seen in FIG. 2, alternative embodiments may include an inclined sliding surface 28 and a corresponding longitudinal slot 29 that are curved and/or that are at an angle with respect to the longitudinal axis 13, such as when viewed from above (i.e., the inclined sliding surface 28 and/or the longitudinal slot 29 can be skewed horizontally with respect to the longitudinal axis 13). Indeed, any configuration of the inclined sliding surface 28 and longitudinal slot 29 is acceptable as long as such configuration permits the slidable member 16 to contact and releasably compress the tubular member 14 during the opening and closing of the catheter valve 10.

Turning now to the internal features of the catheter valve 10, as can be seen in FIGS. 5-7 and 8, which is an exploded view of the catheter valve 10, the tubular member 14 fluidly connects the inlet connector 18 to the outlet connector 20 thereby providing an internal passageway for fluid to flow through the valve body 12 from one end of the catheter valve 10 to the other. The tubular member 14 is a generally resilient flexible or semi-flexible tube that can be selectively fully compressed or released and uncompressed to either permit or restrict fluid flow therethrough. The flexible tubular member 14 may have a generally elongated cylindrical shape formed by walls that allow fluid to pass therethrough; however, other shapes are possible. As used herein the "wall" of the flexible tubular member 14 may refer to the opposing sides of a single flexible tubular member 14 defining a passageway. Thus, reference to "walls of flexible tubular member 14" can refer to opposing sides of a singular cylindrical structure and should not be interpreted as requiring two structurally independent and distinct walls. As will be readily apparent to those skilled in the art, the tubular member 14 need not be tubular in nature (i.e., have a circular cross-section) and may have any geometric shape or construction that provides an internal fluid path for fluid to flow therethrough in an open condition and also permits the internal fluid path to be closed or obstructed upon moving of the slidable member 16 to the closed position, thereby compressing the walls towards each other and restricting flow of a fluid through the catheter valve 10.

Figure 8:
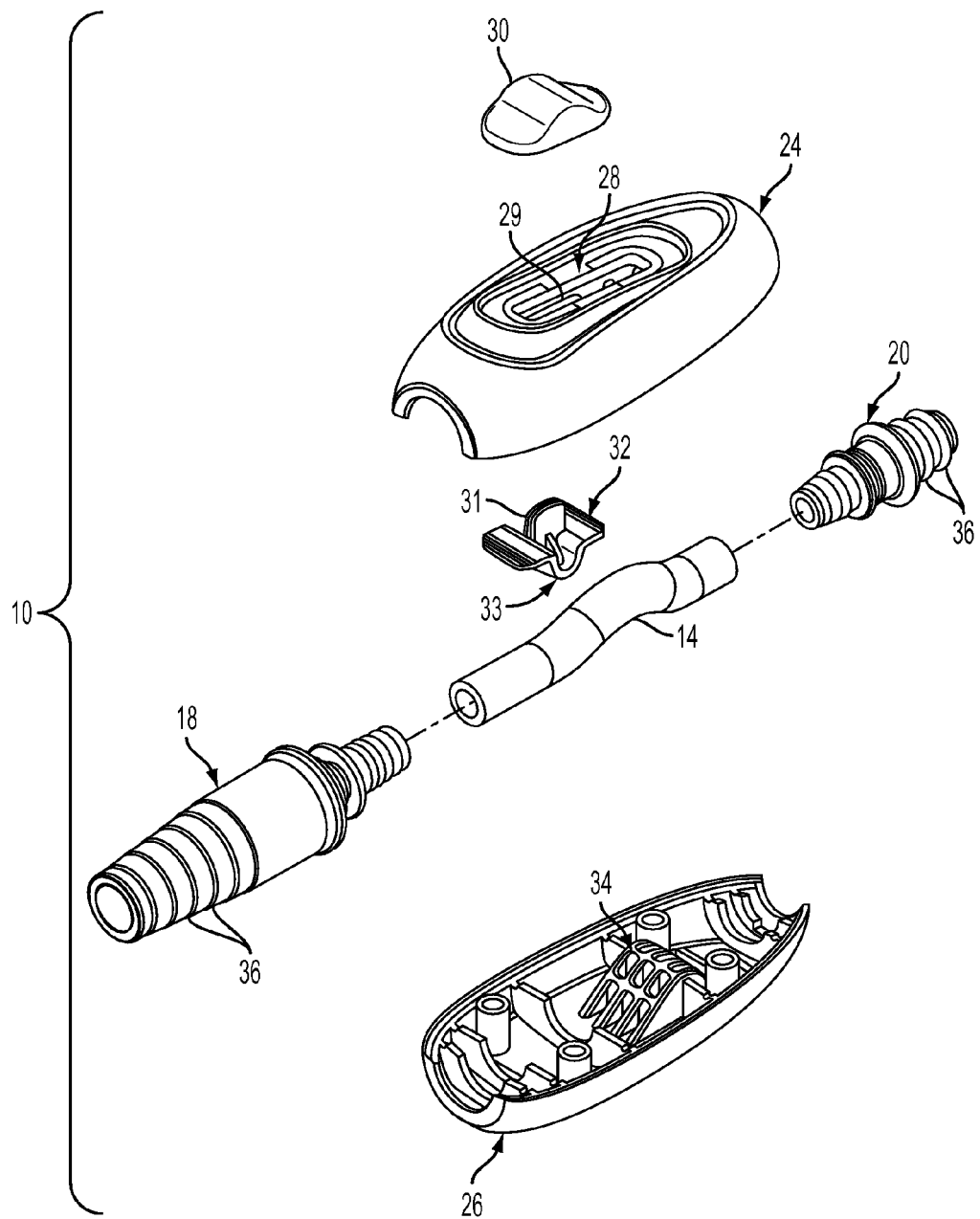
FIG. 8 is an exploded view of the catheter valve depicted in FIG. 1.
Figure 9:
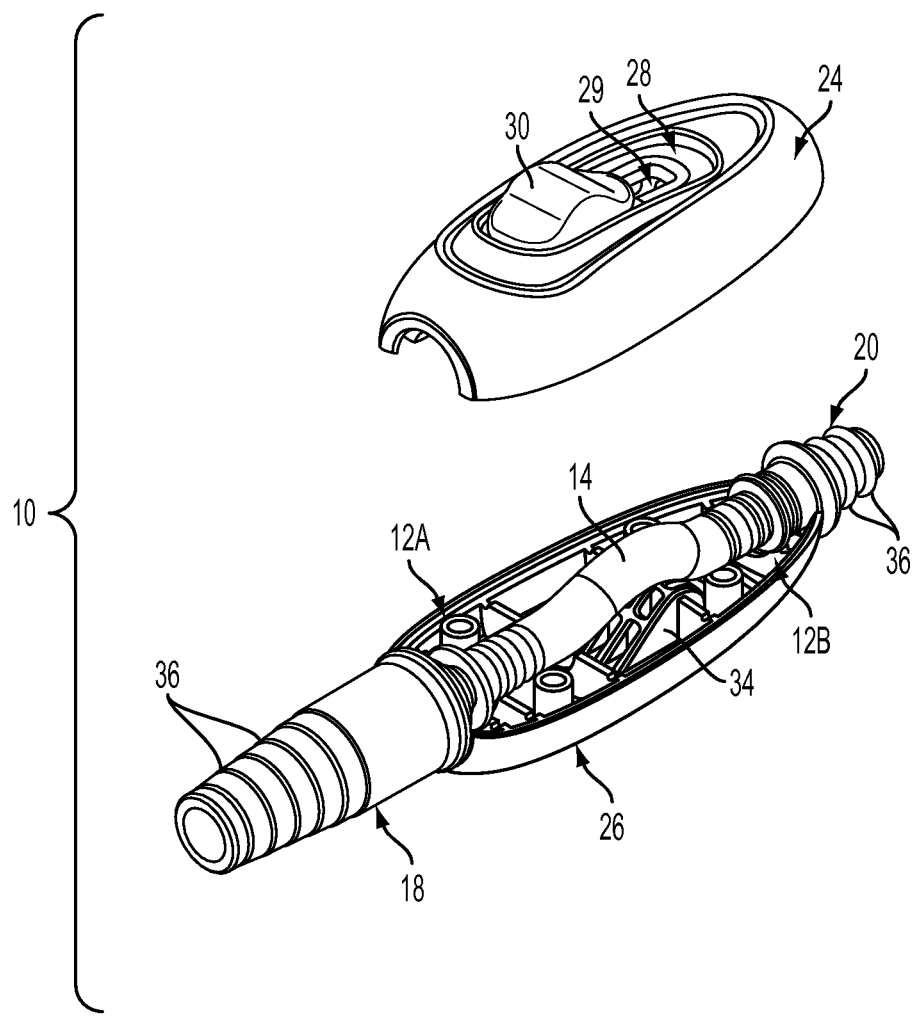
FIG. 9 is a perspective view of the catheter valve depicted in FIG. 1, with the top portion of the valve body removed.
Figure 10:
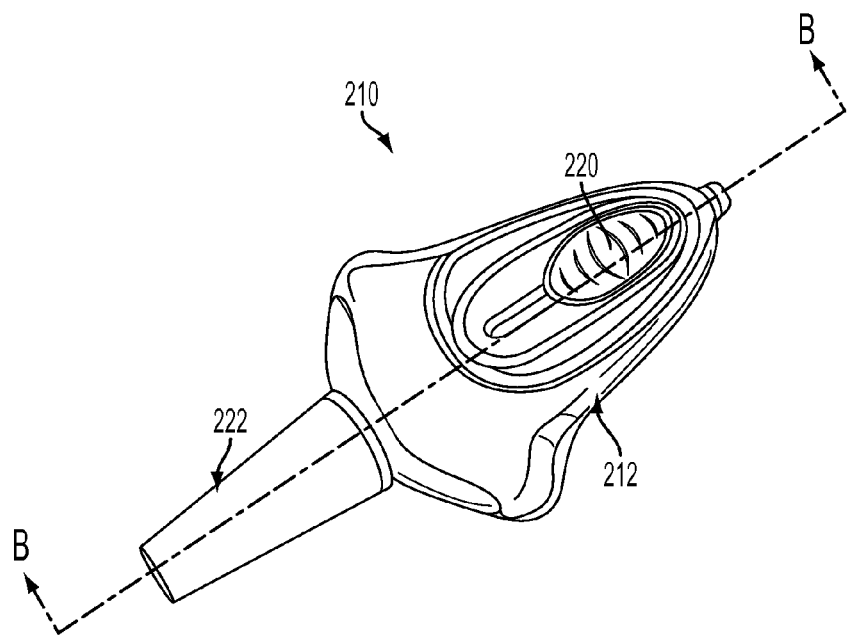
FIG. 10 is a top perspective view of a further exemplary embodiment of a catheter valve.
Figure 11:
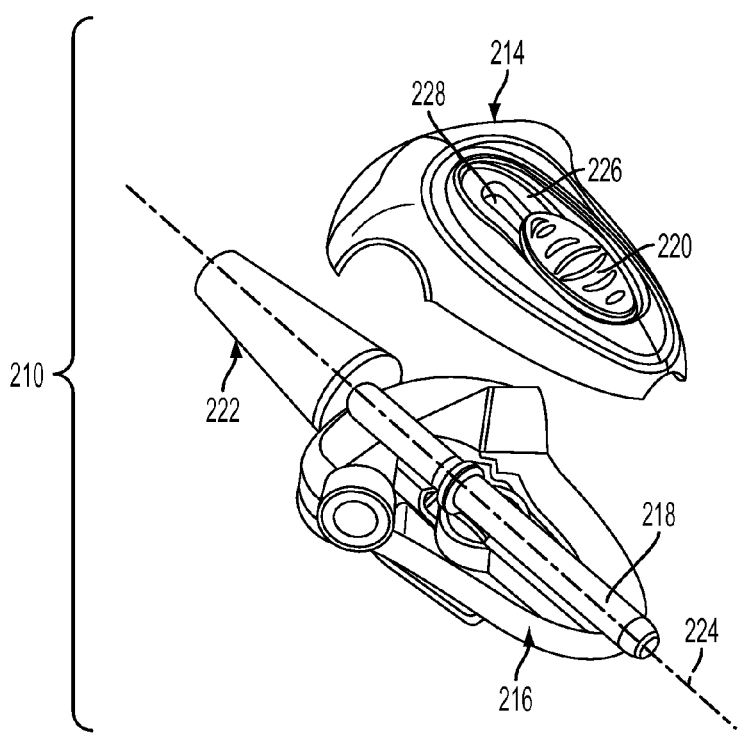
FIG. 11 is a perspective view of the catheter valve depicted in FIG. 10, with the top portion of the valve body removed.
Figure 12:
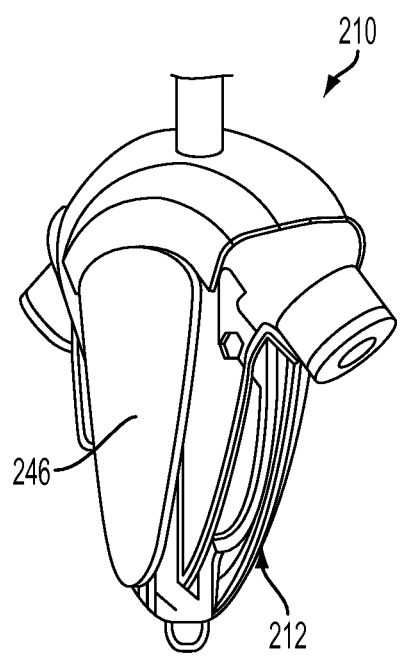
FIG. 12 is a bottom perspective view of the catheter valve depicted in FIG. 10, showing an expandable bellows.

As best seen in FIG. 8, the slidable member 16 may be of a two-piece construction, comprising a sliding top portion 30 and a sliding bottom portion 32 matable thereto. The sliding bottom portion 32, which contacts tubular member 14, includes a curved or convex contact portion 33 that is adapted to minimize piercing or creasing of, or other damage to, the tubular member 14. Moreover, the sliding top portion 30 is designed to have a contour and surface that is easily graspable and manipulable by a user. By way of example, the surface of the sliding top portion 30 may include ridges and/or may be made or coated with a non-slip material.

The sliding top portion 30 and sliding bottom portion 32 may attach to one another via a tab portion 31 that extends through the longitudinal slot 29 in such a manner so that the inclined sliding surface 28 is sandwiched therebetween. The sliding top portion 30 and tab portion 31 of the sliding bottom portion 32 can be attached to each other using a snap- or press-fit connection, friction-fit connection, adhesives, or any other method known in the art. Thus, when the sliding top portion 30 is moved in the longitudinal slot 29 along the inclined sliding surface 28, the sliding bottom portion 32 moves in a corresponding manner. As will be readily apparent to those skilled in the art, the slidable member 16 need not be a multi-component structure but may be of a unitary construction as well.

As can be seen in FIGS. 5-8, the bottom portion 26 of the valve body 12 includes a raised structure 34 such as a ramp or other similar structure extending up from the base of the bottom portion 26. Thus, as can also be seen in the figures, when the tubular member 14 is in place within the valve body 12, at least a portion of the tubular member 14 is disposed along the raised structure 34 between the contact portion 33 of the sliding member 16 and the raised structure 34 of the bottom portion 26 of the valve body 12. As best seen in FIGS. 5, 7 and 8, the flexibility of the tubular member 14 allows the tubular member 14 to bend in order to follow the profile of the raised structure 34. Accordingly, when the sliding member 16 is in the first, open position, position "A," the sliding member 16 and hence, the contact portion 33, is at a point on the inclined surface 28 that is spaced furthest from the base. Thus, the contact portion 33 of the sliding member 16 is at a maximum spacing from the base, with minimal to no engagement the tubular member 14, thereby allowing the lumen or internal passageway of the tubular member 14 to remain generally open and unrestricted, permitting urine to flow through the catheter valve 10. However, as the sliding member 16 is moved along the inclined sliding surface 28 from position "A" to position "B," the contact portion 33 converges toward raised structure 34 on the bottom portion 26 of the valve body 12 thereby compressing the tubular member 14. Thus, as depicted in FIG. 6, when the sliding member 16 is moved entirely to the closed position, the sliding member 16 is at a point "B" on the inclined surface 28 that is closest to the base, compressing the tubular member 14, forcing the interior walls of the lumen into mutual contact with each other thereby fully closing or obstructing the internal passageway of the tubular member 14 and restricting the flow of fluid, such as urine, through the catheter valve 10.

Instead of fully opening or fully closing the catheter valve 10, a user may slide the sliding member 16 to any point along the inclined sliding surface 28 to selectively control the size of the fluid passageway in the lumen of the tubular member 14, thereby controlling the rate at which fluid flows through the catheter valve 10 and hence, the rate at which the bladder empties.

As an alternative to including a raised structure 34, the valve body 12 may be formed without such a structure and instead the tubular member 14 can be disposed within the valve body 12 such that the tubular member 14 remains substantially flat and uncurved (see, e.g., the catheter valve embodiment depicted in FIGS. 13-16). Such a configuration operates similarly, such that, when the slidable member 16 moves from the opened position to the closed position along the inclined sliding surface 28, the slidable member 16 converges toward the bottom portion 26 of the valve body (rather than the raised structure 34) thereby compressing the tubular member 14 and restricting the flow of fluid therethrough.

As depicted in the present embodiment, the inlet connector 18 may be a male fitting with ridges 36 thereon that releasably attaches to the external end of a catheter. The outlet connector 20 may also be a male fitting with ridges 36 thereon that can be used to releasably attach to a collection device such as a urine bag, a drainage tube, a cap or the outlet connector 20 may be left open. Alternatively, although not shown, the inlet and outlet connectors may be female fittings depending on the intended application of the catheter valve 10. The inlet and outlet connectors may be any type of connector that provides for a leak-resistant connection and allows a user to easily attach and detach the catheter valve 10 to a catheter and/or collection or drainage device. Such a connection may be a snap- or press-fit connection, a compression fit or friction fit connection or any other type of connection known in the art. Alternatively, the inlet and outlet connectors need not be separate components and may instead be integrally molded or constructed with the valve body 12, or tubular member 14.

FIGS. 10-16, depict additional exemplary embodiments of a catheter valve 210, which includes a pressure relief valve 244 fluidly connected to a tubular member 218 (see FIGS. 13-16). In use, when the catheter valve 210 is in the closed position, urine will continuously accumulate in the catheter and bladder causing pressure in the bladder to build up. If the pressure is not periodically released, pressure in the bladder may increase to a level that may not be desirable. To avoid such a situation, if pressure reaches certain predetermined levels, the pressure relief valve 244 will actuate to provide a fluid path for the urine to flow from the bladder into a temporary reservoir, thereby lowering the built-up pressure. While the temporary reservoir is not intended as an alternative to periodically opening the catheter valve 210 to void the bladder or using a collection device such as a urine bag, it may serve to prevent accidents, discomfort or other unwanted consequences in the event that pressure builds up in the bladder to undesirable levels.

Similar to the previously disclosed embodiment, the embodiments of a catheter valve 210 depicted in FIGS. 10-16 comprise a valve body 212 having top portion 214, a bottom portion 216, a tubular member 218 defining a lumen therein, a slidable member 220 with a contact portion 221, an inlet connector 222, and a longitudinal axis 224. As can best be seen in FIGS. 13-16, the top portion 214 of the valve body 212 includes an inclined sliding surface 226 with a longitudinal slot 228 therein. The longitudinal slot 228 forms a track 229 in which the slidable member 220 is slidably disposed. Thus, as can best be seen in FIGS. 13-16, the catheter valve 210 opens and closes due to the convergence/divergence of the slidable member 220 toward/from the base 225 of the bottom portion 216 of the valve body 212 as the slidable member 220 slides along the inclined track 229 formed by the longitudinal slot 228 in the inclined sliding surface 226.

More specifically, the contact portion 221 of the slidable member 220 is disposed at a greater distance from the base 225 of the bottom portion 216 when in the first or opened position, position "A," than in the second or closed position, position "B." Accordingly, when the slidable member 220 is moved along the track 229 towards the second position "B," the distance between the contact portion 221 and the base of the bottom portion 216 gradually decreases. As this distance decreases, so does the space between the contact portion 221 and the base 225 with the tubular member 218 therebetween. Thus, as the slidable member 220 moves from position "A" to position "B," the contact portion 221 compresses the tubular member 218. When the distance between the contact portion 221 and the base 225 of the bottom portion 216 is less than that of the diameter of the tubular member 218, the walls of the tubular member 218 are urged into mutual contact with each other until the lumen or internal passageway of the tubular member 218 is fully obstructed or closed as depicted at position "B" in FIGS. 13-16. Thus, when the slidable member 220 is in position "B," the catheter valve 210 is fully closed thereby preventing fluid, such as urine, from flowing therethrough.

As will be readily apparent to those skilled in the art, in all embodiments of the catheter valve 10, 210 disclosed herein, the angle of the inclined sliding 28, 226 surface may be reversed such that the inclined sliding surface 28, 226 is at a minimum height above the interior base of the valve body 12, 212 at position "A" and at a maximum height above the base at position "B." Thus, in this configuration, the catheter valve 10, 210 would be closed when the slidable member 16, 220 is in position "A" and open when the slidable member 16, 220 is in position "B."

Unlike in the previous embodiment of the catheter valve, there is no interior structure included on the base 225 of the bottom portion 216 of the valve body 212 to support the tubular member 218. Therefore, as can be seen in FIGS. 13-16, the tubular member 218 lies flat along the base 225 of the bottom portion 216.

As previously discussed, the present embodiments of the catheter valve include a pressure relief valve 244 to allow attenuation of increased bladder pressure. As can be seen in the figures, the pressure relief valve 244 connects the tubular member 218 to a temporary reservoir. The pressure relief valve 244 can be any type known to those skilled in the art that actuates at a predetermined pressure to open a fluid path to allow urine to flow from the bladder to the temporary reservoir.

Figure 13:
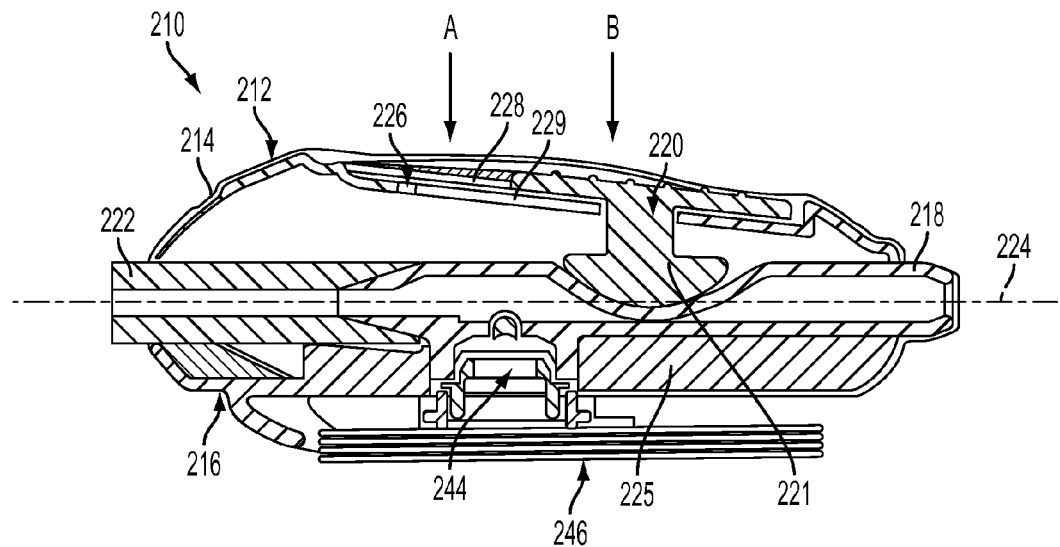
FIG. 13 is a cross-sectional view taken along line B-B in FIG. 10, with an expandable bellows in the unexpanded state.
Figure 14:
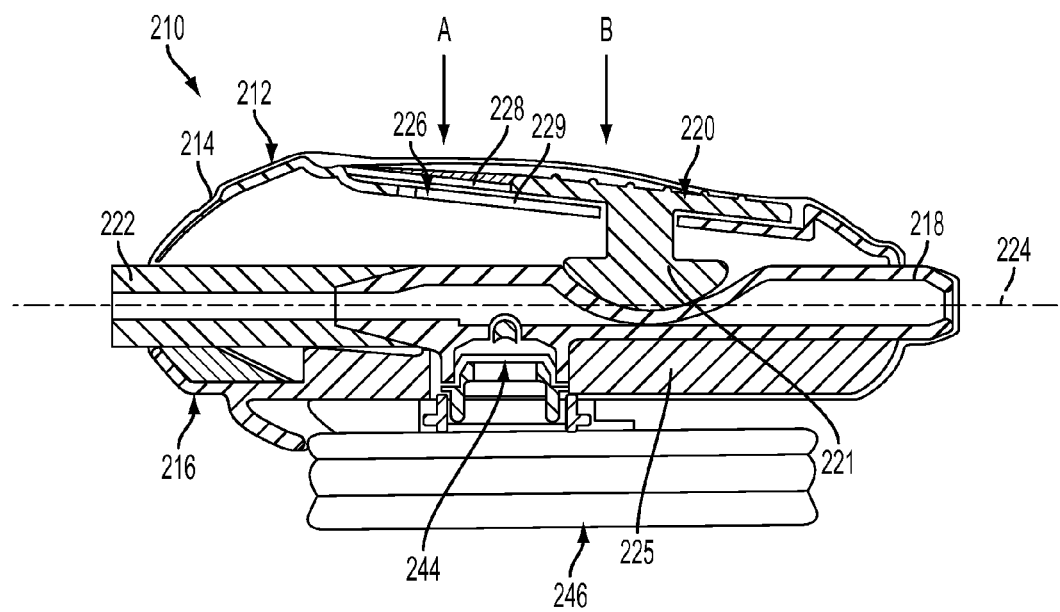
FIG. 14 is a cross-sectional view taken along line B-B in FIG. 10, with an expandable bellows in the expanded state.

In one embodiment, the temporary reservoir can be an expandable bellows 246, which is depicted in FIG. 13 in an unexpanded state, such as prior to actuation of the pressure relief valve 244. If, however, pressure in the bladder was to build to a level above the predetermined actuation pressure level of the pressure relief valve 244, the valve 244 would actuate causing urine to flow through a catheter from the bladder, through the tubular member 218 and the pressure relief valve 244, into the expandable bellows 246 causing the bellows 246 to expand as depicted in FIG. 14.

Figure 15:
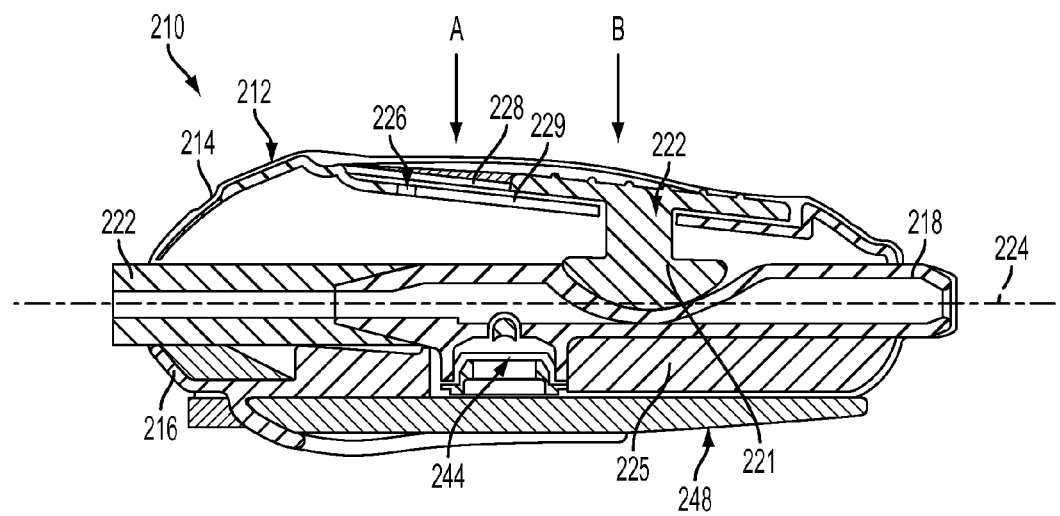
FIG. 15 is a cross-sectional view taken along line B-B in FIG. 10, showing a desiccant pad prior to absorbing a fluid.
Figure 16:
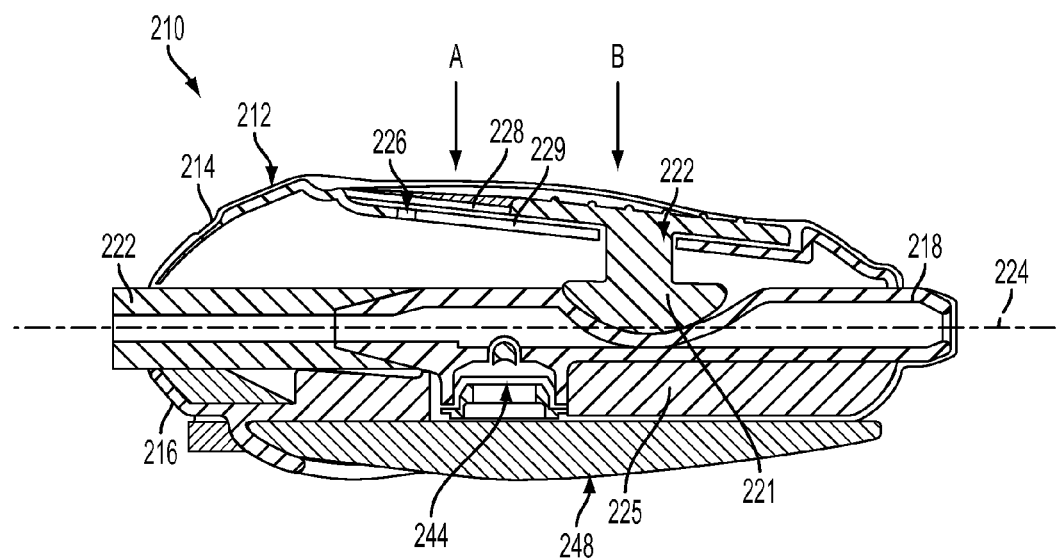
FIG. 16 is a cross-sectional view taken along line B-B in FIG. 10, showing a desiccant pad after absorbing a fluid.

In another embodiment, the temporary reservoir may be a desiccant material, for example, in the form of a desiccant pad 248 as depicted in FIG. 15 in the dry state prior to actuation of the pressure relief valve 244. If, similar to the previous embodiment, pressure in the bladder was to build to a level above the actuation pressure of the pressure relief valve 244, the valve 244 would actuate causing urine to flow through a catheter from the bladder, through the tubular member 218 and the pressure relief valve 244, into the desiccant pad 248 causing the desiccant pad 248 to absorb the urine as depicted in FIG. 16. Examples of desiccant materials may include silica gels, activated clay or molecular sieves.

Figure 17:
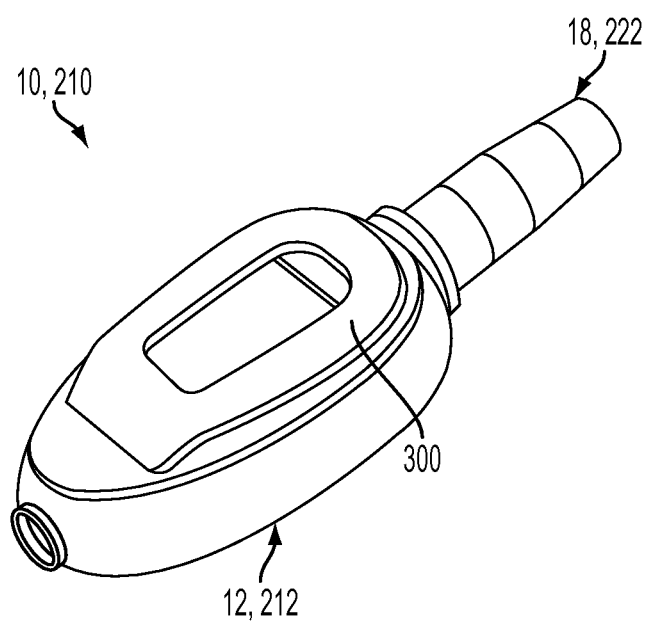
FIG. 17 is a bottom perspective view of a further exemplary embodiment of a catheter valve showing an embodiment of an attachment means.
Figure 18A:
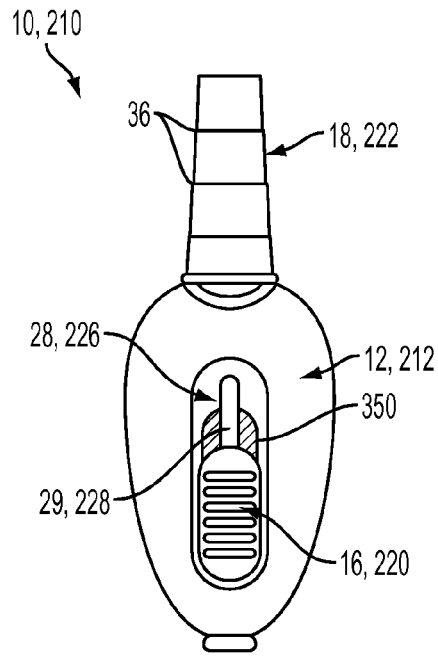
FIG. 18A is a top plan view of a further exemplary embodiment of a catheter valve showing visual markings on the valve body with the catheter valve in the closed position.
Figure 18B:
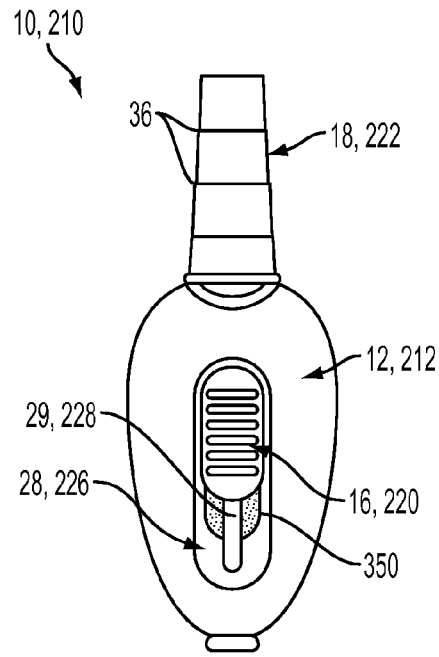
FIG. 18B is a top plan view of a further exemplary embodiment of a catheter valve showing visual markings on the valve body with the catheter valve in the opened position.

As depicted in FIG. 17, any of the previously described embodiments of the catheter valve 10, 210 may also include an attachment means 300 that removeably secures the catheter valve 10, 210 to a user's leg, clothing, or other structure. The attachment means 300 secures the catheter valve 10, 210 and, optionally, any collection device, to allow a user to move about with the catheter valve 10, 210 and any collection device hands-free. For example, the attachment means 300 may include a clip structure, such as the example shown on the external bottom surface of the valve body 12, 212 as shown in FIG. 17. Alternatively, the attachment means 300 may be an adhesive pad, strap or other means for attaching the catheter valve to a body part, clothing or other structure.

The valve body 12, 212, inlet connectors 18, 222 and outlet connector 20, can be constructed from any rigid material such as, for example, rigid polymers including polypropylene, polystyrene, and polyamide. The tubular member 14, 218 can be constructed from any flexible compressible material that maintains a fluid tight passageway during flexing and compression such as, for example, elastomeric polymers including latex, silicone, polyurethane, and polyvinyl chloride. The sliding member 16, 220 can be constructed from any rigid material such as, for example, rigid polymers including polyoxymethylene and polyamide. As will be readily apparent to those skilled in the art, the materials used to construct the catheter valve are not limited to those described above, which are only given by way of example.

Moreover, any of the previously described embodiments of the catheter valve 10, 210 may include additional means to provide a user or caregiver with assurances that the catheter valve 10, 210 is either in the fully opened or fully closed position. In one embodiment, the catheter valve can include a means for producing an audible click, or tactile indication when the slidable member 16, 220 is moved into either the first or open position, position "A" and/or the second or closed position, position "B." The audible click or tactile indication informs the caregiver or user as to whether the slidable member 16, 220 has reached the fully opened position "A" or the fully closed position "B" and thus, whether the catheter valve will permit or restrict the flow of urine.

An example of a way to produce an audible click is depicted in FIGS. 5-7. The sliding bottom portion 32 of the slidable member 16 may include a detent 50 on a first end and a second end. The bottom or interior surface of the inclined sliding surface 28 can include corresponding detents 52 adjacent positions "A" and "B." Thus, when the slidable member 16 is slid to position "A" or "B," the detents 50 on the slidable member 16 move over the detents 52 on the inclined sliding surface 28 thereby producing an audible click informing the user or caregiver that the catheter valve 10, 210 is either in the fully opened or fully closed position. In addition to producing the audible click, the detents can also serve to lock or hold the slidable member 16 in the fully opened or fully closed position.

Figure 19A:
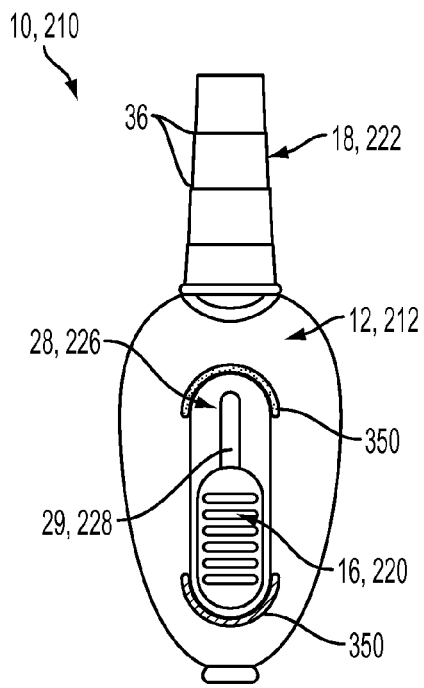
FIG. 19A is a top plan view of a further exemplary embodiment of a catheter valve showing visual markings on the valve body with the catheter valve in the closed position.
Figure 19B:
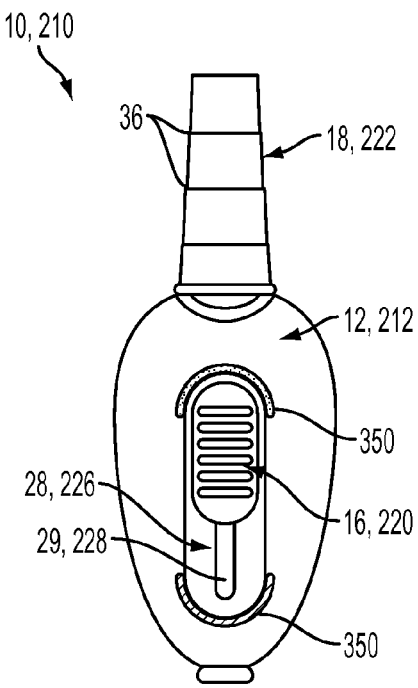
FIG. 19B is a top plan view of a further exemplary embodiment of a catheter valve showing visual markings on the valve body with the catheter valve in the opened position.

Referring now to FIGS. 18A-19B, alternatively, or in combination with audible clicks, the catheter valve 10 may include visual indicators on the valve body 12, 212 that indicates when the slidable member 16, 220 is either (i) in the first or fully opened position, position "A," and/or (ii) in the second or fully closed position, position "B." For example, the valve body 12, 212 may include markings 350 which are of contrasting colors visible against the remainder of the valve body 12, 212, either on the inclined sliding surface 29, 226 (see FIGS. 18A and 18B) or adjacent to the inclined sliding surface 29, 226 (see FIGS. 19A and 19B). For example, green may be included on the valve body 12, 212 to indicate that the catheter valve 10, 210 is in the opened position (see FIGS. 18B and 19B) and red can be included on the valve body 12, 212 to indicate that the catheter valve 10, 210 is in the closed position (see FIGS. 18A and 19A). Additionally or alternatively, the visual indicators included on the valve body 12, 212 may be in the form of the numbers "1" and "0" or the letters "X" and "O" to indicate that the valve 10, 210 is either opened or closed.

Figure 20:
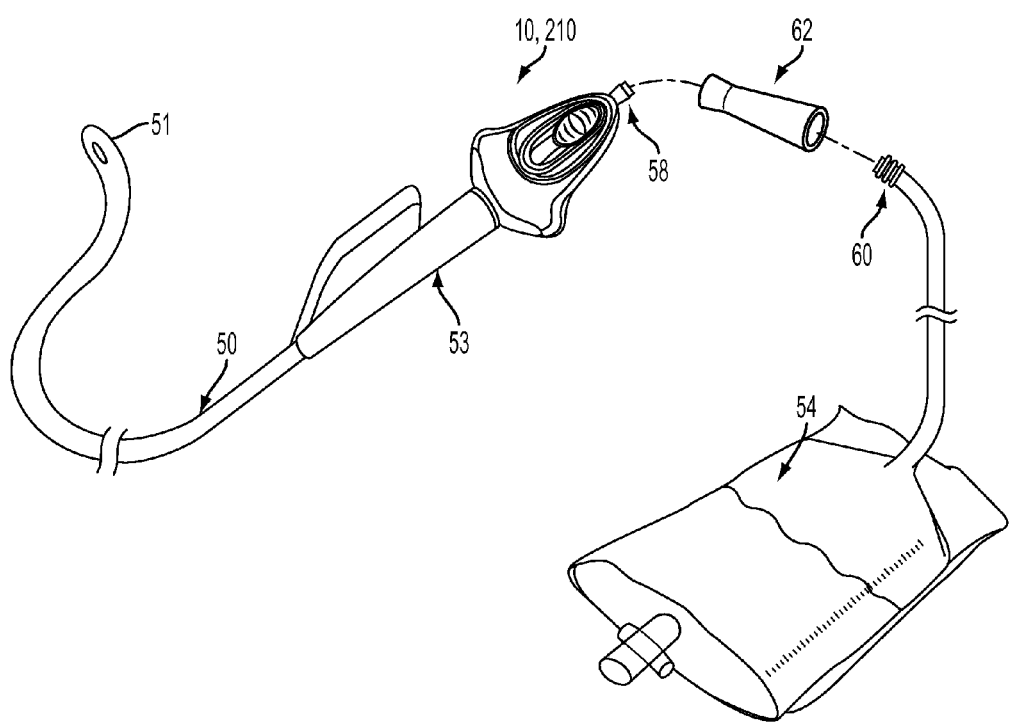
FIG. 20 is a perspective view of an exemplary embodiment of a catheter assembly.

Any embodiments of the catheter valve 10, 210 disclosed or contemplated herein may be provided as a stand-alone device, separately from a catheter, such as a Foley-type catheter, or it may be provided attached to a Foley catheter 56, such as depicted in FIG. 20. As shown, the Foley catheter 56 has a distal end 51 for insertion within a patient's bladder and a proximal end 53 adapted (i) to extend outside of the patient when the distal end 51 is inserted in the patient, and (ii) to couple to the inlet connector 18, 222 of the catheter valve 10, 210. If the catheter valve 10, 210 is provided separately from the Foley catheter 56, the inlet connector 18, 222 of the catheter valve 10 should be connected to the distal end 51 of the Foley catheter 56 prior to insertion of the Foley catheter 56 into the patient in order to prevent leakage of urine from the Foley catheter 56.

As shown in FIG. 20, the catheter valve 10, 210 has a male fitting 58 located at its downstream end. The male fitting is preferred for situations where a user may wish to void their bladder directly into a receptacle, such as a toilet. However, in certain situations, such as at night, users may want to connect the catheter valve 10, 210 to a collection device, such as a urine bag 54, in order to avoid having to periodically void their bladder for an extended period of time. Urine bags that are designed to be mated directly to catheters, such as the Foley catheter 56 shown here, also have a male distal fitting 60 at their distal end, which is adapted to mate to the proximal end 52 of the Foley catheter 56. For such situations, an adapter 62 is provided with two ends configured to mate to the valve 10, 210 and the urine bag 54. As shown in FIG. 20, both ends have female fittings. The distal end 63 is adapted to mate to the male fitting 58 of the catheter valve 10, 210, and the distal end 64 is adapted to distal fitting of a drain bag 54. Once connected to the urine bag 54, the catheter valve 10, 210 may be left in the open position to allow the bladder to drain without a buildup of pressure or the need to periodically travel to a receptacle.

In use, after a Foley catheter 56 is inserted through the urethra and into the bladder of a patient or user, with the catheter valve 10, 210 attached to the Foley catheter 56, a user may freely move around without the need of a collection device such as a urine bag. Instead, the user may periodically void his/her bladder into a receptacle such as, for example, a toilet bowl, by simply grabbing the catheter valve 10, 210 in one hand with his or her thumb positioned on the slidable member 16, 220, directing the catheter valve 10, 210 over the receptacle and moving the slidable member 16, 220 with his/her thumb from position "A" to position "B." When the user is finished voiding the bladder, he/she simply moves the slidable member 16, 220 from position "B" back to position "A" thereby closing the catheter valve 10, 210 and allowing the user to once again freely move around in everyday life.

If the catheter valve 10, 210 is used with a collection device such as a urine bag, as may be the case at night when a user is sleeping, when the urine bag needs to be changed or the user desires to proceed without a urine bag, the user moves the slidable member 16, 220 from position "A" to position "B" thereby closing the catheter valve 10, 210. Once closed, the user can then simply remove the urine bag without spilling or leaking urine. The user can now once again move around freely without a urine bag. Alternatively, the outlet of the catheter valve 10, 210 may also be connected to a drainage tube (not shown), to aid in evacuation of the bladder into a receptacle.

The catheter valve body 10 may be provided individually or in a kit with a Foley catheter and/or a collection device.

Although specific embodiments have been shown and described herein for purposes of illustration and exemplification, it is understood by those of ordinary skill in the art that the specific embodiments shown and described may be substituted for a wide variety of alternative and/or equivalent implementations without departing from the scope of the present invention.

This disclosure is intended to cover any adaptations or variations of the embodiments discussed herein.

We claim:

1. A valve comprising:
    a valve body having a first end, a second end, a longitudinal axis extending between the first end and the second end, and a track having an inclined sliding surface disposed at an angle to the longitudinal axis and having a longitudinal slot therein, the longitudinal slot disposed about a plane containing the longitudinal axis of the valve body and the inclined sliding surface disposed in a plane intersecting the longitudinal axis;
    a tubular member having walls defining a passageway extending through the valve body from the first end to the second end; and
    a slidable member mounted on the track for movement along the inclined sliding surface of the valve body and moveable between a first position and a second position, wherein the first position is a first distance from the longitudinal axis and the second position is a second distance from the longitudinal axis, the first distance being different than the second distance,
    wherein the slidable member is adapted to urge walls of the tubular member towards mutual contact when moved along the inclined sliding surface from the first position to the second position.

2. The valve of claim 1, wherein the slidable member is at least partially disposed within the longitudinal slot and includes an exterior portion adapted to be engaged by a user and an interior contact portion fixedly connected to the exterior portion.

3. The valve of claim 2, wherein as the slidable member is moved from the first position to the second position, the interior contact portion frictionally engages the tubular member, thereby urging the walls of the tubular member towards each other.

4. The valve of claim 2, the valve body further comprising a base located opposite the inclined sliding surface wherein the tubular member is disposed between the interior contact portion of the slidable member and the base.

5. The valve of claim 4, wherein the contact portion of the slidable member is at a maximum spacing with respect to the base at the first position and a minimum spacing with respect to the base at the second position.

6. The valve of claim 4, wherein the base further comprises a protrusion extending towards the track.

7. The valve of claim 6, wherein sliding the slidable member from the first position to the second position causes the contact portion of the slidable member to engage the tubular member, thereby urging the walls of the tubular member towards each other.

8. The valve of claim 7, wherein the walls of the tubular member are urged into mutual contact with each other when the slidable member is in the second position thereby obstructing the lumen and restricting flow of a fluid through the valve.

9. The valve of claim 1, wherein the angle of the inclined sliding surface with respect to the longitudinal axis is approximately 3-9°.

10. The valve of claim 1, further comprising a pressure sensitive valve fluidly connected to the tubular member.

11. The valve of claim 10, wherein the pressure sensitive valve is fluidly connected to a temporary reservoir.

12. The valve of claim 11, wherein the temporary reservoir is selected from the group consisting of an expandable bellows and a desiccant pad.

13. The valve of claim 1, wherein movement of the slidable member to either the first position or the second position is denoted by an indicator.

14. The valve of claim 13, wherein the indicator is selected from the group consisting of an audible click, a tactile indicator or a visual indicator.

15. The valve of claim 1, wherein the valve body further comprises a visual indicator that indicates when the slidable member is in the first position or the second position.

16. A urinary catheter valve for controlling flow of urine from a bladder, the catheter valve comprising:
    a valve body having an inlet end, an outlet end, a base, a longitudinal axis extending between the inlet end and the outlet end, and a track having an inclined sliding surface disposed at an angle to the longitudinal axis and having a longitudinal slot therein, the longitudinal slot being disposed about a plane that contains the longitudinal axis;
    a tubular member having a lumen therein with walls defining a passageway extending through the valve body from the inlet end to the outlet end; and
    a slidable member mounted on the inclined sliding surface of the track and operable between a first position and a second position along the inclined surface, wherein the first position is a first distance from the longitudinal axis and the second position is a second distance from the longitudinal axis that is different than the first distance,
    wherein the slidable member is adapted to urge walls of the tubular member towards mutual contact when moved along the inclined sliding surface from the first position to the second position to control the flow of urine through the catheter valve.

17. The catheter valve of claim 16, wherein the valve body further comprises an interior structure extending inwardly from a base of the valve body into an interior of the valve body opposite the slidable member.

18. The catheter valve of claim 17, wherein the slidable member includes an exterior portion fixedly joined to an interior contact portion.

19. The catheter valve of claim 16, wherein the slidable member is at least partially disposed within the longitudinal slot, and wherein the slidable member slides from the first position to the second position in the longitudinal slot along the inclined sliding surface, wherein in the first position the slidable member is a first distance from the longitudinal axis and in the second position the slidable member is a second distance from the longitudinal axis, the second distance being less than the first distance.

20. The catheter valve of claim 16, wherein the slidable member is at a maximum spacing with respect to the base at the first position and a minimum spacing with respect to the base at the second position.

21. The catheter valve of claim 16, wherein the contact portion of the slidable member converges toward the interior structure of the valve body and frictionally engages the tubular member as the slidable member moves from the first position to the second position.

22. The catheter valve of claim 17, wherein the flexible tubular member is at least partially disposed between the interior structure and the interior contact portion of the slidable member.

23. The catheter valve of claim 22, wherein moving the slidable member from the first position to the second position causes the contact portion of the slidable member to compress the tubular member, thereby urging the walls of the tubular member towards each other.

24. The catheter valve of claim 23, wherein the walls of the tubular member are urged into mutual contact with each other when the slidable member is in the second position thereby obstructing the lumen and preventing flow of a fluid through the valve.

25. The catheter valve of claim 16, wherein the angle of the inclined sliding surface with respect to the longitudinal axis is approximately 3-9°.

26. The catheter valve of claim 16, further comprising a pressure sensitive valve that fluidly connects the tubular member to a temporary reservoir.

27. The catheter valve of claim 16, wherein movement of the slidable member to either the first position or the second position produces an indication selected from the group consisting of an audible click, a tactile indication or a visual indication.

28. The catheter valve of claim 16, wherein the tubular member comprises a flexible material.

29. The catheter valve of claim 16, further comprising an inlet connector at the inlet end.

30. The catheter valve of claim 29, wherein the inlet connector is adapted to connect to a Foley catheter.

31. The catheter valve of claim 16, wherein when the slidable member is in the first position, the catheter valve is open and when the slidable member is in the second position, the catheter valve is closed.

32. The catheter valve of claim 16, wherein the valve body is a multi-component structure comprising a top portion and a bottom portion.

33. The catheter valve of claim 16, further comprising an attachment means for securing the catheter valve to a user.

34. A kit comprising the catheter valve of claim 16 and a Foley catheter.

35. A catheter assembly comprising:
    a catheter having a proximal end for insertion within a patient and a distal end adapted to extend outside of the patient when the proximal end is inserted into the patient; and
    a catheter valve comprising:
    a valve body having an inlet end fluidly connected to the distal end of the catheter, an outlet end, a longitudinal axis extending between the inlet end and the outlet end, and a track having an inclined sliding surface disposed at an angle to the longitudinal axis and having a longitudinal slot therein, the longitudinal slot being disposed about a plane that contains the longitudinal axis and the inclined sliding surface;
    a tubular member having a lumen therein with walls defining a passageway extending through the valve body from the inlet end to the outlet end; and
    a slidable member mounted on the inclined sliding surface of the valve body and moveable between a first position and a second position, wherein the first position is at a first distance from the longitudinal axis and the second position is at a second distance from the longitudinal axis and the first and second distances are different,
    wherein the slidable member is adapted to urge walls of the tubular member towards mutual contact when moved along the inclined sliding surface from the first position to the second position to control the flow of urine through the catheter valve.

36. The catheter assembly of claim 35, wherein the catheter is a Foley catheter.

37. The catheter assembly of claim 35, further comprising a collection device for collection of urine that flows through the catheter valve.

38. The catheter assembly of claim 37, further comprising a collection device having a first collection end and an adaptor having first and second adaptor ends, wherein the first adaptor end is configured to mate with the outlet end of the valve body and the second adapter end is configured to mate with the first collection end.

39. The catheter assembly of claim 36, wherein the slidable member is at least partially disposed within the longitudinal slot and comprises an exterior portion adapted to be engaged by a user and an interior contact portion fixedly connected to the exterior portion, and wherein the interior contact portion frictionally engages the tubular member as the slidable member is moved from the first position to the second position.

\* \* \* \* \*